United States Patent [19]

Kennedy et al.

[11] Patent Number: 5,618,790
[45] Date of Patent: Apr. 8, 1997

[54] PROTEASE MEDIATED DRUG DELIVERY SYSTEM

[75] Inventors: James C. Kennedy, Kingston; Michel Ringuet, Trois Rivieres; Roy H. Pottier, Kingston, all of Canada

[73] Assignee: Queen's University at Kingston, Kingston, Canada

[21] Appl. No.: 213,897

[22] Filed: Mar. 16, 1994

Related U.S. Application Data

[63] Continuation-in-part of Ser. No. 833,183, Feb. 10, 1992, abandoned, which is a continuation-in-part of Ser. No. 593,867, Oct. 5, 1990, abandoned.

[51] Int. Cl.$^6$ .......................... A61K 37/36; A61K 38/00; C07K 13/00
[52] U.S. Cl. ................... 514/12; 514/16; 514/17; 514/18; 530/321; 530/324; 530/328
[58] Field of Search .................. 514/16–18, 12; 530/328, 321, 324

[56] References Cited

PUBLICATIONS

Isonnguth et al., Biochimica et Biophysica Acta 924 pp. 19–26 (1987).
Keller et al. Macromolecules, 23, pp. 428–311 (1990).
Sezaki et al. Crit. Rev. Ther. Drugs Carrier Syst.. 1(1), pp. 1–38 (1984).

*Primary Examiner*—Howard E. Schain
*Assistant Examiner*—Lynn Touzeau
*Attorney, Agent, or Firm*—Richard J. Hicks

[57] ABSTRACT

Lipophilic and amphiphilic therapeutic or diagnostic agents having water solubilizing groups attached thereto by bonds that can be cleaved readily by one or more of the various proteases that are active in the extracellular fluid or on the surfaces of cells in many types of malignant tissue may accumulate selectively in such malignant tissues. Protease mediated removal of the water solubilizing groups converts such drugs into lipophilic or amphiphilic forms which are more soluble in plasma membrane lipids and which therefore enter cells more readily. Since the extracellular fluid in most non-malignant tissues under normal circumstances has little such protease activity, removal of the water solubilizing groups takes place primarily within malignant tissues, with consequent preferential accumulation of the lipophilic or amphiphilic forms of the drug within malignant tissues. Certain lipophilic and amphiphilic porphyrins and chlorins may be modified by the addition of water solubilizing groups, such as alcohols, which are attached by short polypeptide chains, that are stable while in the circulation but are cleaved by proteases in malignant tissue to provide novel compounds useful for the photodynamic therapy of cancer.

10 Claims, No Drawings

PROTEASE MEDIATED DRUG DELIVERY SYSTEM

CROSS REFERENCE TO RELATED APPLICATION

This is a continuation in part of our earlier filed U.S. application Ser. No. 07/833,183 filed Feb. 10, 1992, which now abandoned, which in turn is a continuation in part of application Ser. No. 07/593,867 filed 5 Oct.1990 and now abandoned.

FIELD OF INVENTION

This invention relates to a novel concept and technique for the chemical modification of lipophilic and amphiphilic drugs to increase their selective accumulation at the site of tissue abnormalities due to malignancy; of bacterial, fungal, protozoal or parasitic infection, or other tissue injuries and intravascular or extravascular clotting, to a novel class of compounds having therapeutic and diagnostic properties, to a method of making same, and to a method for treating or identifying said abnormalities in patients in need thereof.

BACKGROUND OF INVENTION

Every cytotoxic agent used in the treatment of cancer causes damage to normal as well as malignant cells. The maximum therapeutically useful dose is limited by toxicity to essential normal tissues, and in many cases it is not possible to give a dose large enough to destroy the cancer without also killing the patient. However, if the concentration of the cytotoxic drug could be increased in the malignant tissues only, then the therapeutic effectiveness of the drug would be increased without a corresponding increase in toxicity.

Certain types of tissue abnormalities, disease processes, and infections are characterized by abnormally high levels of activity of specific extracellular and/or intracellular proteases. To date, at least 144 different types of proteases had been identified in mammalian cells. Other types of protease are produced by various pathogenic bacteria, fungi, protozoa, or parasites. It has become clear that proteases play a key regulatory role in a great variety of intracellular and extracellular processes. In addition to their well-known digestive functions in the stomach and intestine, proteases are involved in the coagulation process, complement activation, fertilization, tissue remodelling during growth and development, the activation of other enzymes, and the formation and release of a wide variety of peptide hormones.

As might be expected in view of their important role in the regulation of mammalian cell functions, the activity of certain intracellular and extracellular proteases can be altered by disease processes that involve tissue injury, necrosis, inflammation, repair, or degeneration. Abnormally high activities of certain specific proteases are present at the sites of physical or chemical trauma, blood clots, malignant tumors, rheumatoid arthritis, inflammatory bowel disease, gingival disease, glomerulonephritis, and acute pancreatitis. Abnormal protease activity occurs in disseminated intravascular coagulation, and is suspected to be involved in the development of liver fibrosis, pulmonary emphysema, atherosclerosis, and muscular dystrophy. Consequently, attempts have been made (with some success) in both patients and experimental animals to retard the progression of some of these diseases by the administration of appropriate protease inhibitors.

Various pathogenic bacteria, fungi, and protozoa secrete unique proteases. Consequently, localized infections may be associated with a localized concentration of specific protease activity. Cells involved in the reaction of the host cells against such infections also secrete proteases.

Thus, there is need for a therapy that is designed to make use of the abnormally high levels of activity of specific types of extracellular proteases that characterize certain tissue abnormalities, disease processes, and infections. In summary, instead of attempting to block the activity of such proteases, use is made of their activity to induce a preferential accumulation of selected therapeutic and/or diagnostic compounds at the extracellular site of the abnormal activity.

Increasing the cellular or tissue specificity of a therapeutic or diagnostic agent will improve its therapeutic ratio and/or the sensitivity of detection or visualization of certain types of lesions. Although localized disease processes may lead to a wide range of systemic abnormalities, usually the primary goal of treatment is to bring the localized disease under control. Under most conditions the therapeutic effectiveness of a given agent is directly related to its concentration in the diseased cells or tissues, while its systemic toxicity is related to its concentration in various susceptible cells and tissues in other parts of the body. Consequently, it may be predicted that the maximum safe dose (and therefore the therapeutic effectiveness) of a given agent will increase without a corresponding increase in systemic toxicity if that agent can be made more specific for its target cells or tissues. An increase in specificity is of particular value for agents whose therapeutic effectiveness is limited at present by serious systemic toxicity.

Certain radiolabelled or fluorescent compounds such as dihematoporphyrin ether that show a useful degree of specificity for certain types of cellular or tissue abnormalities are used clinically at present to detect and/or visualize those abnormalities. Any significant improvement in the specificity of such compounds for the lesions in question will improve the sensitivity of the technique.

OBJECT OF INVENTION

It is, therefore, an object of the present invention to provide novel drugs by providing lipophilic and amphiphilic drugs with appropriate water solubilizing groups linked thereto by bonds that can be cleaved readily by one or more of the proteases that are present in the extracellular fluid or on the surface of cells in many types of damaged, abnormal or infected tissues, which accumulate selectively in said tissues.

BRIEF STATEMENT OF INVENTION

By one aspect of this invention there is provided a method for treating or detecting tissue abnormalities caused by malignancy; bacterial, fungal, protozoal and parasitic infections; tissue injuries and intravascular and extravascular clotting abnormalities, in a patient comprising administering to said patient an effective amount of a lipophilic or amphiphilic compound having water solubilizing groups attached thereto by bonds cleavable by a protease present at the site of said abnormality, so as to cause selective accumulation of said compound at the site of said abnormality.

By another aspect of this invention there is provided a method for treating malignant tissue abnormalities in a patient comprising administering to said patient an effective amount of a lipophilic or amphiphilic compound having water solubilizing groups attached thereto by bonds cleavable by a protease present in said malignant tissue, so as to cause selective accumulation of said compound in said malignant tissue.

By yet another aspect of this invention there is provided a conjugate system for delivering a therapeutic or diagnostic agent to a tissue abnormality site in a patient, comprising: a selected lipophilic or amphiphilic said agent; a protease sensitive polypeptide, having an amino acid sequence readily cleavable by a protease active at said tissue abnormality site but not readily cleavable by a protease active at a normal tissue site, covalently linked to said agent; and a solubility modifier conjugated to said protease sensitive polypeptide.

DETAILED DESCRIPTION OF PREFERRED EMBODIMENTS

It is known that as malignant tumors enlarge from a single cell to a palpable nodule, their growth pattern is such that certain areas of tumor develop an inadequate blood supply. The cells in such zones are both poorly nourished and hypoxic. Some of these cells die, but other merely reduce their metabolic activity to a basal level. Such cells are relatively resistant to destruction by X-rays and gamma-rays, since (i) molecular oxygen is required for some of the radiation chemistry that can cause DNA damage and cell death, and (ii) quiescent cells are relatively resistant to radiation damage. Hypoxic and poorly nourished cells tend to be resistant to many types of chemotherapeutic agents also. Chemotherapeutic agents usually enter tissues via the blood, and malignant cells whose blood supply is inadequate may not receive a lethal dose. In addition the toxicity of many common chemotherapeutic agents is restricted primarily to cells that are in cell cycle (cycle specific agents). Consequently, malignant cells that are poorly nourished and/or hypoxic may survive courses of radiotherapy and/or chemotherapy that otherwise might have been curative. Such surviving cells may proliferate subsequently to cause a recurrence of the cancer.

One obvious solution to this problem is to increase the concentration of a radiomimetic chemotherapeutic agent in the malignant cells by increasing its concentration in the circulation. However, in many cases, it is not possible to increase the concentration of the drug in the circulation without causing an unacceptable level of toxicity to the patient. This applies to both cycle-specific and radiomimetic chemotherapeutic agents. Another possible solution is to increase the specificity of the drug for the malignant tissue.

In the absence of active transport, most organic compounds enter cells only after dissolving in the lipids of the plasma membrane. However, the lipid/water partition coefficient of many organic compounds is highly dependent upon their state of ionization. Organic compounds tend to remain in solution in the extracellular fluid (aqueous phase) if highly ionized, but to dissolve in the plasma membranes (lipid phase) if nonionized or electrically neutral.

A series of compounds has been designed that are highly ionized or otherwise hydrophilic while in the blood and extracellular fluid of most normal tissues, but which become relatively lipophilic when specific peptide linkages in those compounds are cleaved by proteases that are active in the extracellular environment or on the surface of cells at the sites of certain types of tissue pathology. Such compounds will tend to accumulate preferentially at those sites of pathology.

The degree of specificity of the compound for the target cell or tissue will depend upon (i) the specificity of the protease in question for the compound's peptide linkage, and (ii) the ratio of the activity of that protease at the site of the abnormality to its activity on various normal cells or in various normal tissues. The greatest site specificity will be obtained if the protease is highly specific for the substrate and if it is either absent or inactive or normal cells and in normal tissues.

The targets for protease-directed diagnosis and/or therapy include but are not limited to certain types of malignant tumors, certain types of infections (bacterial, fungal, protozoal, and parasitic), localized sites of tissue injury from various other causes, and localized sites of intravascular or extravascular clotting. The abnormal protease activity that makes possible the preferential accumulation of a given compound may be (i) in the extracellular fluid, (ii) in exudate, pus, or areas of tissue necrosis, and (iii) on the external surface of plasma membranes or other biological structures that are in direct contact with the extracellular fluid.

Each compound has three functionally distinct components.

(1) An active component—This may be lipophilic or amphiphilic. The active component may include but is not limited to:

(a) fluorescent or radiolabelled compounds that can help identify or visualize sites of tissue abnormality, or (b) selected compounds of therapeutic value (radioactive, photosensitizing, immunostimulatory, chemotherapeutic, antitumor, anti-bacterial, anti-fungal, or anti-viral). Examples of active compounds include but are not limited to commercially available carboxylic acid porphyrins listed below.

uroporphyrin III
uroporphyrin I
heptacarboxylporphyrin I
hexacarboxylporphyrin I
pentacarboxylporphyrin I
coproporphyrin I
coproporphyrin III
protoporphyrin IX
deuteroporphyrin IX, 2,4-disulfonic acid
deuteroporphyrin IX, 2,4-bis glycol
hematoporphyrin IX
deuteroporphyrin IX, 2-vinyl 4-hydroxymethyl
deuteroporphyrin IX, 2,4 (4,2) hydroxyethyl vinyl
deuteroporphyrin IX
mesoporphyrin IX All of these porphyrins include at least two alkane side chains, each of which is terminated by a carboxylic acid group. Such carboxylic acid groups are used to link protease-cleavable peptide chains to the "active component" via amide bonds or other appropriate linkages.

(2) A solubility modifier—This consists of one or more molecules of a relatively non-toxic hydrophilic or amphiphilic compound linked via a specific peptide chain to each molecule of active component.

The hydrophillic solubility modifiers include but are not limited to:

(a) compounds bearing one or more acidic and/or basic groups whose dissociation constants are such that they show significant ionization within the normal range of physiological pH. These may be sulfonic acids, carboxylic acids, or amines.

(b) compounds bearing one or more hydroxyl groups whose dissociation constants are such that they are not ionized within the usual physiological range of pH. These include ethyl alcohol, glycerol, glucose, galactose, inositol, mannitol, glactitol, adonitol and arabitol, gluconic acid, and glucoheptonic acid, either as single molecules or as multiple molecules forming sidechains attached to a linear or branched backbone, and amino and carboxylic acid derivatives thereof.

The lipophilic solubility modifiers include but are not limited to:

(a) non-ionizable compounds bearing one or more aliphatic or aromatic hydrocarbon groups.

(b) polypeptide chains whose ionizable group have been blocked by lipophilic groups.

Examples of solubility modifiers include poly-L-lysine, poly-D-lysine, and poly D, L-lysine which can be linked via an amide bond to the protease-sensitive polypeptide. This adds multiple primary amino groups to the compound and thus increases its solubility in water, especially at the somewhat acid pH of the extracellular fluid that characterizes most malignant tissues.

The polylysine also provides a backbone of reactive amino groups to which multiple copies of molecules of other solubility modifiers can be attached via amide bonds or other appropriate linkage. Such molecules may carry groups that at physiological pH are either highly ionized (sulfonic acids), partially ionized (carboxylic acids), or non-ionized but hydrophilic (hydroxyl groups).

(3) A peptide chain which links the active component to the solubilizer(s). The amino acid sequence of the chain is such that it can be cleaved readily under physiological conditions by specific proteases that are normally active in the extracellular fluid or on surfaces at the site of the lesion in question. However, its sequence is such that it is not cleaved readily by the proteases that might be active at comparable sites on normal cells or in normal tissues. Since different types of lesions are characterized by different types of protease which have different substrate specificities, the amino acid sequence of the peptide chain that links the active component to the solubilizer varies according to the type of lesion that is intended as the target. For example, compounds that are designed to accumulate preferentially in nodules of carcinoma of the breast may be given a polypeptide chain that is as specific as possible for collagenase type IV (gelatinase A), since this protease normally is quite active in the extracellular environment of such tumors.

The nature of the bond between the protease-cleavable polypeptide chain(s) and each molecule of active compound will vary with the type of reactive groups that can be used or induced on the active component without causing a significant loss of its activity. For example, if carboxylic acids or primary amino groups are present and can be used without harm to the "active component", then the polypeptide chain(s) will be attached via peptide bonds. Certain unsaturated double bonds, hydroxyl groups, carbonyl groups, or sulfhydryl groups may offer other sites for linkage without loss of function. Similar considerations govern the choice of the bond between the polypeptide chain and the solubility modifier. However, ester linkages will not be used for either purpose unless the ester bond can be protected by a bulky group that blocks the action of the esterases which are universally present in normal blood and extracellular fluid.

Examples of synthetic polypeptide chains that can be cleaved by proteases known to be active in and/or immediately adjacent to certain specified cell or tissue abnormalities, include:

(a) Substrates for human interstitial collagenase, also known as mammalian matrix metalloproteinase-1 (MMP-1)

—Pro—Gln—Gly—Ile—Ala—Gly—Gln—Arg—(SEQ ID NO: 1)

—Pro—Gln—Gly—Leu—Ala—Gly—Gln—Arg— (SEQ ID NO: 2)

This protease is active against collagens of Types I, II, and III. It is unusually active in the extracellular environment of several different types of human tumors, including carcinoma of the stomach, both adenocarcinoma and squamous cell carcinoma of the lung, carcinoma of the pancreas, and malignant melanoma. It cleaves between the glycine and the leucine or isoleucine.

(b) A substrate for bacterial collagenase from *C. histolyticum* (Clostridiopeptidase A)s —Leu—Gly—Pro—Ala—(SEQ ID NO: 3)

This protease is present in tissues infected with *C. histolyticum*. Cleavage is between the leucine and the glycine.

(c) A substrate for bacterial collagenase from *Achromobacter isophagus*

—Pro—Leu—Gly—Pro—Arg—(SEQ ID NO: 4)

This protease is secreted by *Achromobacter isophagus*. Cleavage is between the leucine and the glycine.

(d) Substrates for cathepsin D

—Phe—Gly—His—Phe—Phe—Val—Leu—(SEQ ID NO: 5)

—Arg—Gly—Phe—Phe—Leu—(SEQ ID NO: 6)

—Phe—Ala—Ala—Phe—Phe—Val—Leu—(SEQ ID NO: 7)

—Phe—Ala—Ala—Phe—Phe—Leu—Val—(SEQ ID NO: 8)

Cathepsin D normally is an intracellular enzyme, but it is secreted and activated in the extracellular space in numerous human malignant tissues, including many carcinomas of the breast. Cleavage is between the two phenylalanines.

(e) Some substrates for plasmin

—Val—Leu—Lys—(SEQ ID NO: 9)

—Val—Leu—Arg—(SEQ ID NO: 10)

—Gly—Pro—Lys—(SEQ ID NO: 11)

—Gly—Pro—Arg—(SEQ ID NO: 12)

—Ala—Phe—Lys—(SEQ ID NO: 13)

—Ala—Phe—Arg—(SEQ ID NO: 14)

Plasmin is a protease with a fairly board specificity. It appears to be activated in a cascade reaction by several different cathepsins and urokinase-like plasminogen activator.

(f) Substrate for human collagenase Type IV (also known as 72 kD gelatinase, mammalian matrix proteinase-2, or MMP2).

—Pro—Leu—Gly—Pro—Arg—(SEQ ID NO: 4)

—Gly—Pro—Leu—Gly—Pro—(SEQ ID NO: 15)

This proteinase is active against collagen Type IV. There is strong evidence that it is involved in the erosion of malignant tumors through basement membranes and adjacent normal tissues. Human tumors that show an abnormally high activity of collagenase Type IV include carcinomas of the colon, kidney, breast, prostate, liver, bladder, lung, pancreas, ovaries, and stomach; Kaposi's sarcoma, fibrosarcoma, malignant melanoma, and Hodgkin's lymphoma.

In order to illustrate this invention in more detail, in vitro and in vivo studies were conducted using a synthetically constructed bioactive molecule designed to accumulate preferentially at sites of extracellular collagenase activity. This molecule comprised three functionally distinct parts:

(a) Mesoporphyrin IX, a compound which is poorly soluble in most aqueous solutions at physiological pH. It is strongly fluorescent when completely dissolved (monomeric) but only weakly fluorescent when not completely dissolved (aggregated).

(b) A synthetic polypeptide (Lys—Lys—Lys—Lys) (SEQ ID NO: 16), which is highly soluble in blood, lymph, and most other body fluids at physiological Ph.

(c) A synthetic polypeptide (Gly—Pro—Leu—Gly—Pro—Ala) (SEQ ID NO: 17), which forms a collagenase-sensitive linkage between the insoluble mesoporphyrin and the soluble (Lys—Lys—Lys—Lys) (SEQ ID NO: 16) polypeptide.

The carboxyl group of the alanine (Ala) of the collagenase-sensitive linkage was covalently joined to the (Lys—Lys—Lys—Lys) (SEQ ID NO: 16) via a peptide bond. The amino group of the glycine (Gly) of the collagenase-sensitive linkage was covalently joined to each propionic acid side chain of the mesoporphyrin via an amide bond. This is, each molecule of mesoporphyrin carried two propionic acid side chains, both of which were linked with (Lys—Lys—Lys—Lys) (SEQ ID NO: 16) via a collagenase-sensitive polypeptide as described above.

The overall configuration of the molecule is summarized below.

mesoporphyrin IX (Gly—Pro—Leu—Gly—Pro—Ala—Lys—Lys—Lys—Lys)$_2$ (SEQ ID NO: 18)

EXAMPLE 1

The molecule described above was synthesized using an applied Biosystems Model 431A peptide synthesizer with standard Fmoc reagents and techniques. The only deviation from standard practice involved the use of a 1:1 mixture of dimethylformamide and dimethylsulfoxide (DMF and DMSO) to dissolve the mesoporphyrin IX, since this particular porphyrin is poorly soluble in N-methylpyrrolidone (NMP), the usual solvent.

The compound was purified by HPLC and its predicted molecular mass was verified by mass spectrometry. The observed molecular mass was 2574.8, and the predicted value 2577.3, a deviation which is far too small to be caused by a discrepancy from the predicted structure.

The purified compound was a purple-red powder that was quite soluble in water in neutral pH, in isotonic saline for injection (U.S.P.), and in fresh heparinized human blood and plasma. Aqueous solutions were strongly fluorescent when exposed to 410 nm light. The emission spectrum showed a typical porphyrin fluorescence pattern.

EXAMPLE 2

The enzyme specificity of the linkage was evaluated by mixing an aqueous solution of the compound with aqueous solutions of selected enzymes and then measuring changes in the porphyrin fluorescence over time. Since mesoporphyrin is almost insoluble in water at physiological pH and is only weakly fluorescent when aggregated, enzymatic cleavage of the mesoporphyrin IX moiety from its two solubilizing polypeptides (Lys—Lys—Lys—Lys) (SEQ ID NO: 16) might be expected to cause a great decrease in the solubility of the mesoporphyrin with a consequent decrease in fluorescence. That is, enzymes that have an affinity for the collagenase-sensitive polypeptide that links the mesoporphyrin with the solubilizing group (Lys—Lys—Lys—Lys) (SEQ ID NO: 16) will cause a rapid decrease in fluorescence, while enzymes that have little or no affinity for that particular polypeptide will not.

Experiment—The concentration of the stock solution of porphyrin compound was 0.02 mg/ml of water. The concentration of the stock solution of each enzyme was 2.0 mg/ml of water. These stock solutions were mixed in a 1:1 ratio (0.5 ml/0.5 ml) to produce a mixture containing 0.01 mg porphyrin and 1.0 mg enzyme per ml of solution.

Results for room temperature incubation are tabulated below.

| Enzyme | Time to decrease in fluorescence (visual observation) |
| --- | --- |
| water | control |
| papain (Sigma P-3125) | no decrease in 30 minutes |
| chymotrypsin Type II (Sigma C4128) | no decrease in 30 minutes |
| protease XIV (Sigma P-5147) | approximately 3 minutes |
| pepsin A (BDH 3.4.23.1) | between 5 and 10 minutes |
| protease V (Sigma P-5005) | approximately 2.5 minutes |
| trypsin (Difco 0152-13) | approximately 4 minutes |
| pronase (B grade, Calbiochem) | approximately 3 minutes |
| protease (grade II, Dispase, B-M) | between 5 and 10 minutes |
| collagenase 1A (Sigma C-9891) | less than 5 seconds |
| collagenase IV (Sigma C-5138) | less than 5 seconds |

The porphyrin fluorescence in each mixture was then quantitated by spectrophotofluorometer. This reads in relative fluorescence units, with a maximum (saturation level) of 16,000.

| Enzyme | Incubation time = 90 minutes |
| --- | --- |
| Water | 15,775 fluorescence units |
| papain (Sigma P-3125) | 16,383 |
| chymotrypsin Type II (Sigma C4128) | 15,188 |
| protease XIV (Sigma P-5147) | 2,725 |
| pepsin A (BDH 3.4.23.1) | 2,610 |
| protease V (Sigma P-5005) | 1,512 |
| trypsin (Difco 0152-13) | 1,169 |
| pronase (B grade, Calbiochem) | 2,314 |
| protease (grade II, Dispase, B-M) | 2,248 |
| collagenase 1A (Sigma C-9891) | 879 |
| collagenase IV (Sigma C-5138) | 658 |

The fluorescence measurements were repeated at intervals for up to 24 hours. The only significant change during that time was a slow decrease in porphyrin fluorescence in the chymotrypsin mixture.

The porphyrin fluorescence was largely restored following the addition of an equal volume of 8 molar urea. This indicates that the mesoporphyrin moiety of the molecule had not been destroyed by treatment with collagenase or other enzymes, but had merely been aggregated.

Thus, it can be seen in vitro that, as predicted above, the interaction of the porphyrin compound with collagenase caused a rapid and substantial decrease in porphyrin fluorescence, whereas the interaction of the porphyrin compound with enzymes having other specificities did not cause such a rapid or such a profound loss of porphyrin fluorescence. It is concluded, therefore, that the synthetic molecule shows substantial specificity for collagenase 1A and collagenase IV, and this is compatible with the postulated mechanism, i.e. the polypeptide that links the mesoporphyrin moiety with the solubilizing group (Lys—Lys—Lys—Lys) (SEQ ID NO: 16) was cleaved by collagenase in a relatively enzyme specific manner, thus separating the relatively insoluble mesoporphyrin end of the molecule from its solubilizer. Subsequent aggregation of the porphyrin led to loss of the porphyrin fluorescence.

EXAMPLE 3

*Clostridium perfringens* synthesizes and secretes large amounts of collagenase in addition to several other proteolytic enzymes. When *C. perfringens* is grown on blood agar, these enzymes diffuse out to produce a zone of hemolysis about each colony.

Colonies of *C. perfringens* were overlaid on blood agar with an aqueous solution of the porphyrin compound (0.02 mg/ml) of Example 1.

Within less than 1 minute, the original strong porphyrin fluorescence was greatly diminished within the zones of hemolysis about each colony, but was not diminished where there was no hemolysis.

It should be noted that the presence of intact erythrocytes in the agar might be expected to diminish the amount of fluorescence, since hemoglobin absorbs the near UV light used to induce fluorescence, and erythrocytes as such would scatter it. However, the decrease in fluorescence was instead in the hemolysed area, where light transmission was much better.

This observation is compatible with the proposed mechanism—that the collagenase-sensitive linkage between the porphyrin moiety and its solubilizer had been cleaved by the enzymes that had diffused out from each colony of *C. perfringens*, thus allowing the relatively insoluble porphyrin moiety to aggregate and leading to the observed loss of porphyrin fluorescence.

EXAMPLE 4

Aliquots of the porphyrin compound of Example 1 were added to heparinized whole blood and plasma samples which were then examined by spectrophotofluorometer. No effect on fluorescence intensity was noted, from which it is concluded that the enzymes in blood do not cleave the collagenase sensitive peptide.

EXAMPLE 5

The porphyrin compound of Example 1 was injected intraperitoneally into mice at dosages up to 20 mg/kg body weight. No toxic effects were observed.

EXAMPLE 6

Mice were injected intradermally with *Clostridium perfringens* and after an incubator period of 24 hours, were injected intraperitoneally with 20 mg/kg body weight of the porphyrin compound of Example 1. Porphyrin fluorescence in normal skin and at sites of intradermal injectin was then quantitated by spectrophotofluorometer. Porphyrin fluorescence increased by a factor of three, relative to the background fluorescence, at the injection site of the *Clostridium perfringens*. It is hypothesized that the reason for the increase in porphyrin fluorescence is that the collagenase at the infection site, which contains an excess of extracellular collagenase, traps (by binding and/or cleaving) the porphyrin compound from the circulation and causes accumulation of the porphyrin at the infection site.

---

We claim:

1. A conjugate system for delivering a therapeutic or diagnostic agent to a tissue abnormality site in a patient, comprising:
   a selected lipophilic or amphiphilic said agent;
   a protease sensitive polypeptide, having an amino acid sequence readily cleavable by a protease active at said tissue abnormality site but not readily cleavable by a protease active at a normal tissue site, covalently linked to said agent; and
   a solubility modifier conjugated to said protease sensitive polypeptide.

2. A system according to claim 1 wherein said selected lipophilic or amphophilic agents are carboxylic acid porphyrins.

3. A system according to claim 2 wherein said porphyrins are selected from the group consisting of
   uroporphyrin III
   uroporphyrin I
   heptacarboxylporphyrin I
   hexacarboxylporphyrin I
   pentacarboxylporphyrin I
   coproporphyrin I
   coproporphyrin III
   protoporphyrin IX
   deuteroporphyrin IX, 2,4-disulfonic acid
   deuteroporphyrin IX, 2,4-bis glycol
   hematoporphyrin IX
   deuteroporphyrin IX, 2-vinyl 4-hydroxymethyl
   deuteroporphyrin IX, 2,4 (4,2) hydroxyethyl vinyl
   deuteroporphyrin IX, and
   mesoporphyrin IX.

4. A system as claimed in claim 1 wherein said solubility modifier is a hydrophilic solubility modifier selected from the group consisting of sulfonic acids, carboxylic acids, amines, ethyl alcohol, glycerol, glucose, galactose, inositol, mannitol, glactitol, adonitol, arabitol, gluconic acid, glucoheptonic acid and amino and carboxylic acid derivatives thereof.

5. A system according to claim 4 wherein said polypeptide is selected from the group consisting of:

—Pro—Gln—Gly—Ile—Ala—Gly—Gln—Arg—(SEQ ID NO: 1),

—Pro—Gln—Gly—Leu—Ala—Gly—Gln—Arg— (SEQ ID NO: 2),

—Leu—Gly—Pro—Ala—(SEQ ID NO: 3),

—Pro—Leu—Gly—Pro—Arg—(SEQ ID NO: 4),

—Phe—Gly—His—Phe—Phe—Val—Leu—(SEQ ID NO: 5),

—Arg—Gly—Phe—Phe—Leu—(SEQ ID NO: 6),

—Phe—Ala—Ala—Phe—Phe—Val—Leu—(SEQ ID NO: 7),

—Phe—Ala—Ala—Phe—Phe—Leu—Val—(SEQ ID NO: 8),

—Val—Leu—Lys—(SEQ ID NO: 9),

—Val—Leu—Arg—(SEQ ID NO: 10),

—Gly—Pro—Lys—(SEQ ID NO: 11),

—Gly—Pro—Arg—(SEQ ID NO: 12),

—Ala—Phe—Lys—(SEQ ID NO: 13),

—Ala—Phe—Arg—(SEQ ID NO: 14),

—Gly—Pro—Leu—Gly—Pro—(SEQ ID NO: 15), and

—Gly—Pro—Leu—Gly—Pro—Ala—(SEQ ID NO: 17).

6. A system according to claim 1 wherein said solubility modifier is selected from the group consisting of substituted and unsubstituted lysines.

7. A system as claimed in claim 1 wherein said solubility modifier contains at least one solubilizing group selected from sulfonic acids, carboxylic acids, amines, and alcohols.

8. A system as claimed in claim 6 wherein said poly lysine is selected from poly-L-lysine, poly-D-lysine, and poly D, L-lysine.

9. A system according to claim 7 wherein said solubility modifier is selected from the group consisting of amino acids, polypeptide and alcohols.

10. A system as claimed in claim 9 wherein said alcohol is selected from the group ethyl alcohol, glycerol, glucose, galactose, inositol, mannitol, glactitol, adonitol, arabitol, gluconic acid, glucopheptonic acid and amino and carboxylic acid derivatives thereof.

* * * * *

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION:8
        ( D ) OTHER INFORMATION:/product= "OTHER"
          / note= "Carboxy terminus is amidated."

( x i ) SEQUENCE DESCRIPTION: SEQ ID NO: 1:

Pro  Gln  Gly  Ile  Ala  Gly  Gln  Arg
    1                       5

( 2 ) INFORMATION FOR SEQ ID NO: 2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site ( B ) LOCATION:8
        ( D ) OTHER INFORMATION:/product= "OTHER"
            / note= "Carboxy terminus is amidated."

( x i ) SEQUENCE DESCRIPTION: SEQ ID NO: 2:

Pro  Gln  Gly  Leu  Ala  Gly  Gln  Arg
    1                     5

( 2 ) INFORMATION FOR SEQ ID NO: 3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 3:

Leu  Gly  Pro  Ala
    1

( 2 ) INFORMATION FOR SEQ ID NO: 4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 4:

Pro  Leu  Gly  Pro  Arg
    1                     5

( 2 ) INFORMATION FOR SEQ ID NO: 5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 5:

Phe  Gly  His  Phe  Phe  Val  Leu
    1                     5

( 2 ) INFORMATION FOR SEQ ID NO: 6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 6:

Arg  Gly  Phe  Phe  Leu
    1                     5

( 2 ) INFORMATION FOR SEQ ID NO: 7:

( i ) SEQUENCE CHARACTERISTICS:
        ( A ) LENGTH: 7 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO: 7:

Phe Ala Ala Phe Phe Val Leu
1               5

(2) INFORMATION FOR SEQ ID NO: 8:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 8:

Phe Ala Ala Phe Phe Leu Val
1               5

(2) INFORMATION FOR SEQ ID NO: 9:

(i) SEQUENCE CHARACTERISTICS:
(A) LENGTH: 3 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 9:

Val Leu Lys
1

(2) INFORMATION FOR SEQ ID NO: 10:

(i) SEQUENCE CHARACTERISTICS:
(A) LENGTH: 3 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 10:

Val Leu Arg
1

(2) INFORMATION FOR SEQ ID NO: 11:

(i) SEQUENCE CHARACTERISTICS:
(A) LENGTH: 3 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 11:

Gly Pro Lys
1

(2) INFORMATION FOR SEQ ID NO: 12:

(i) SEQUENCE CHARACTERISTICS:
(A) LENGTH: 3 amino acids
(B) TYPE: amino acid
(C) STRANDEDNESS: single ( D ) TOPOLOGY: linear ( i i ) MOLECULE TYPE: peptide ( x i ) SEQUENCE DESCRIPTION: SEQ ID NO: 12:

Gly Pro Arg
1

( 2 ) INFORMATION FOR SEQ ID NO: 13:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 13:

Ala Phe Lys
1

( 2 ) INFORMATION FOR SEQ ID NO: 14:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 14:

Ala Phe Arg
1

( 2 ) INFORMATION FOR SEQ ID NO: 15:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 15:

Gly Pro Leu Gly Pro
1               5

( 2 ) INFORMATION FOR SEQ ID NO: 16:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 16:

Lys Lys Lys Lys
1

( 2 ) INFORMATION FOR SEQ ID NO: 17:

( i ) SEQUENCE CHARACTERISTICS:
( A ) LENGTH: 6 amino acids
( B ) TYPE: amino acid
( C ) STRANDEDNESS: single (D) TOPOLOGY: linear (ii) MOLECULE TYPE: peptide (xi) SEQUENCE DESCRIPTION: SEQ ID NO: 17:

Gly Pro Leu Gly Pro Ala
1               5

(2) INFORMATION FOR SEQ ID NO: 18:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 18:

Gly Pro Leu Gly Pro Ala Lys Lys Lys Lys
1               5                   10